(12) United States Patent
Ullberg et al.

(10) Patent No.: US 7,333,590 B2
(45) Date of Patent: Feb. 19, 2008

(54) DUAL-SOURCE SCANNING-BASED DETECTION OF IONIZING RADIATION

(75) Inventors: Christer Ullberg, Sollentuna (SE); Tom Francke, Sollentuna (SE)

(73) Assignee: XCounter AB, Danderyd (SE)

( * ) Notice: Subject to any disclaimer, the term of this patent is extended or adjusted under 35 U.S.C. 154(b) by 0 days.

(21) Appl. No.: 11/447,900

(22) Filed: Jun. 7, 2006

(65) Prior Publication Data

US 2007/0223653 A1  Sep. 27, 2007

(30) Foreign Application Priority Data

Mar. 21, 2006  (SE)  ................ 0600636

(51) Int. Cl.
*G01N 23/087*  (2006.01)
(52) U.S. Cl. ................ 378/62; 378/22
(58) Field of Classification Search .......... 378/37–39, 378/55, 62, 196, 205, 21–27
See application file for complete search history.

(56) References Cited

U.S. PATENT DOCUMENTS

| | | | |
|---|---|---|---|
| 4,637,040 A | 1/1987 | Sohval et al. | |
| 4,686,695 A | 8/1987 | Macovski | |
| 6,337,482 B1 | 1/2002 | Francke | |
| 6,370,223 B1 | 4/2002 | Gleason et al. | |
| 6,476,397 B1 | 11/2002 | Francke | |
| 6,477,223 B1 | 11/2002 | Francke | |
| 6,522,722 B1 | 2/2003 | Francke | |
| 6,627,897 B1 | 9/2003 | Francke et al. | |
| 6,784,436 B2 | 8/2004 | Francke | |
| 6,794,656 B2 | 9/2004 | Francke et al. | |
| 6,818,901 B2 | 11/2004 | Francke et al. | |
| 6,856,669 B2 | 2/2005 | Francke et al. | |
| 6,873,682 B2 | 3/2005 | Francke et al. | |

(Continued)

FOREIGN PATENT DOCUMENTS

DE  44 06 958  9/1995

(Continued)

OTHER PUBLICATIONS

International-Type Search Report dated Sep. 20, 2006 for corresponding Swedish Application No. 0600636-5.

(Continued)

*Primary Examiner*—Hoon Song
(74) *Attorney, Agent, or Firm*—Harness, Dickey & Pierce, P.L.C.

(57) ABSTRACT

A dual-source scanning-based radiation detecting apparatus comprises at least two radiation sources provided for emitting ionizing radiation of optionally different energies, direction sensitive line detectors arranged in an array, and a device for scanning the line detectors across an object to be examined. The line detectors are alternately pointing towards different ones of the radiation sources. The device for scanning is arranged for keeping the line detectors aligned during scanning to enable each of the line detectors to record multiple line images of the object. The scanning is preferably performed at least a distance corresponding to N times the distance between two adjacent ones of the line detectors, where N is the number of the radiation sources, to thereby enable recording of line images sufficient to form a two-dimensional image of the object at each of the different energies.

26 Claims, 5 Drawing Sheets

U.S. PATENT DOCUMENTS

| | | |
|---|---|---|
| 6,940,942 B2 | 9/2005 | Ullberg |
| 6,970,533 B2 | 11/2005 | Francke et al. |
| 7,006,597 B2 | 2/2006 | Francke |
| 7,016,458 B2 | 3/2006 | Francke |
| 7,027,561 B2 | 4/2006 | Francke et al. |
| 2003/0155518 A1 | 8/2003 | Francke |
| 2005/0067570 A1 | 3/2005 | Retterath et al. |
| 2005/0096853 A1 | 5/2005 | Hansen |
| 2005/0135550 A1 | 6/2005 | Man et al. |
| 2005/0226367 A1 | 10/2005 | Francke |
| 2005/0226368 A1 | 10/2005 | Francke |
| 2006/0039532 A1* | 2/2006 | Wu et al. ............ 378/62 |
| 2006/0210016 A1* | 9/2006 | Francke ............ 378/22 |

FOREIGN PATENT DOCUMENTS

| | | |
|---|---|---|
| EP | 0 231 037 | 8/1987 |
| GB | 2 287 164 | 9/1995 |

OTHER PUBLICATIONS

International-Type Search Report dated Jul. 6, 2007 for corresponding Swedish Application No. PCT/SE2007/000239.

* cited by examiner

DUAL-SOURCE SCANNING-BASED DETECTION OF IONIZING RADIATION

PRIORITY STATEMENT

This application claims priority under 35 U.S.C. § 119 to Swedish Patent Application No. 0600636-5, filed on Mar. 21, 2006, in the Swedish Patent and Registration Office, the entire contents of which are incorporated herein by reference.

FIELD OF THE INVENTION

The invention relates generally to apparatuses and methods for dual-source scanning-based detection of radiation.

BACKGROUND OF THE INVENTION AND RELATED ART

Various line detectors for detecting ionizing radiation are known in the art. While such detectors provide for instantaneous one-dimensional imaging, two-dimensional imaging can only be performed by means of scanning the line detector, and optionally the radiation source, in a direction traverse to the one-dimensional detector array. Such scanning-based detection may be time consuming. Movement of the object being examined may occur during scanning, which would severely reduce the image quality obtained.

There are also known dual-energy detectors in the art, i.e. detectors, with which two images are produced using radiation of different energy and combined into a single image to enhance different elements in the image. Generally attenuation is a function of x-ray energy according to the two attenuation mechanisms photoelectric absorption and Compton scattering. These two mechanisms differ among materials of different atomic numbers. For this reason, measurements at two energies can be used to distinguish between different elements.

Dual-energy x-ray techniques can be used to identify bone tissue separately from soft tissue in medical imaging, for example, or to identify hazardous materials, for example, in baggage scanning.

SUMMARY OF THE INVENTION

A main object of the invention is to provide a dual-source scanning-based ionizing radiation detecting apparatus and method, which provides for the recording of two-dimensional images of high spatial and temporal resolution.

In this respect there is a particular object to provide such an apparatus and such a method, which are uncomplicated and can produce dual-source high-quality two-dimensional images with excellent, signal-to-noise ratio, dynamic range, and image contrast.

A further object of the invention is to provide such an apparatus and such a method, by which dual-energy radiation detection ca be made.

A yet further object of the invention is to provide such an apparatus and such a method, by which the elemental composition of an object that is detected can be revealed.

A still further object of the invention is to provide such an apparatus and such a method, which enable a fast scanning across the object to be examined.

A yet further object of the invention is to provide such an apparatus and such a method, which are reliable, accurate, and inexpensive.

These objects, among others, are attained by apparatuses and methods as claimed in the appended claims.

According to one aspect of the invention there is provided a dual-source scanning-based radiation detecting apparatus comprising at least two radiation sources, a plurality of direction sensitive line detectors arranged in an array, and a device for scanning the line detectors across an object to be examined. According to the invention the line detectors in the array are alternately pointing towards different radiation sources, and the device for scanning keeps the line detectors aligned with the radiation sources during scanning to enable each of the line detectors to record a plurality of line images of the object. Hereby, additional information about the object may be revealed, particularly in the direction along the radiation.

A high temporal resolution is obtained since the line detectors in the array are alternately pointing towards different radiation sources.

In one embodiment the radiation sources create ionizing radiation of different energies, and scanning is performed at least a distance corresponding to N times the distance between two adjacent line detectors, where N is the number of the radiation sources, to thereby enable recording of line images sufficient to form a two-dimensional image of the object at each of the different energies. That is, if N=2 the scanning is performed at least twice the distance between two adjacent line detectors.

This aspect of the invention provides for a flexible solution where the different energies can be freely chosen since different radiation sources are provided for the different energies.

In another embodiment the radiation sources create ionizing radiation of similar energy, and scanning is performed a distance so that each of the line detectors is scanned across the entire object to obtain, for each of the line detectors, a two-dimensional image of radiation as transmitted through the object in a respective one of a plurality of different angles. This image data may be used in a tomosynthesis reconstruction process.

The radiation sources are preferably spaced apart in a direction essentially parallel with the scanning direction, which may be in the X direction. However, they may alternatively and/or additionally be spaced apart in a direction essentially perpendicular thereto, e.g. essentially parallel with the extension of each line detector, i.e. in the Y direction. Hereby, the spatial resolution may be improved in a direction essentially perpendicular to both those direction, i.e. the Z direction, which coincides with the depth of the images recorded.

A similar improvement may be obtained also when the radiation sources are spaced apart in the X direction only, by increasing the distance between the radiation sources (in contrast to what is normally desired). Thus, adjacent radiation sources are spaced apart by at least 0.2 degrees, preferably at least 5 degrees, more preferably at least 30 degrees, and most preferably at least 60 degrees, as seen from the detector.

According to another aspect of the invention there is provided a dual-energy scanning-based radiation detecting apparatus comprising at least two radiation sources provided for emitting ionizing radiation, a plurality of direction sensitive line detectors arranged in at least two arrays, and a device for scanning the line detectors across an object to be examined. According to the invention the radiation sources create ionizing radiation of different energies, the line detectors in a first one of the arrays are pointing towards a first one of the radiation sources and the line detectors in a second one of the arrays are pointing towards a second one of the two radiation sources, and the device for scanning keeps the line detectors aligned with the radiation sources during scanning to enable each of the line detectors to record a plurality of line images of the object. Each of the line detectors is scanned across the entire object to thereby enable recording of line images sufficient to form multiple two-dimensional images of the object at each of the different energies.

This aspect of the invention provides for a solution where several two-dimensional images at each radiation source energy may be recorded with high temporal resolution.

In one embodiment the arrays of line detectors are arranged on a support which, together with the radiation sources, is, during scanning, rotated in a plane whose normal is parallel with the propagation direction of the ionizing radiation of different energies as created by the radiation sources. Hereby, a high number of two-dimensional images may be recorded at each radiation source energy simply by rotating the support with the arrays of line detectors and the radiation sources at constant rotational speed.

The one-dimensional detector unit is preferably, but not exclusively, a gaseous based parallel plate detector unit. Other detector units that may be used include diode arrays, scintillator based arrays, CCD arrays, TFT- and CMOS-based detectors, liquid detectors, and solid-state detectors, e.g. one-dimensional PIN-diode arrays with edge-on, near edge-on or perpendicular incidence of X-rays.

Further characteristics of the invention and advantages thereof, will be evident from the detailed description of preferred embodiments of the present invention given hereinafter and the accompanying FIGS. 1-5, which are given by way of illustration only and thus, are not limitative of the present invention.

DESCRIPTION OF PREFERRED EMBODIMENTS

Figure 1:
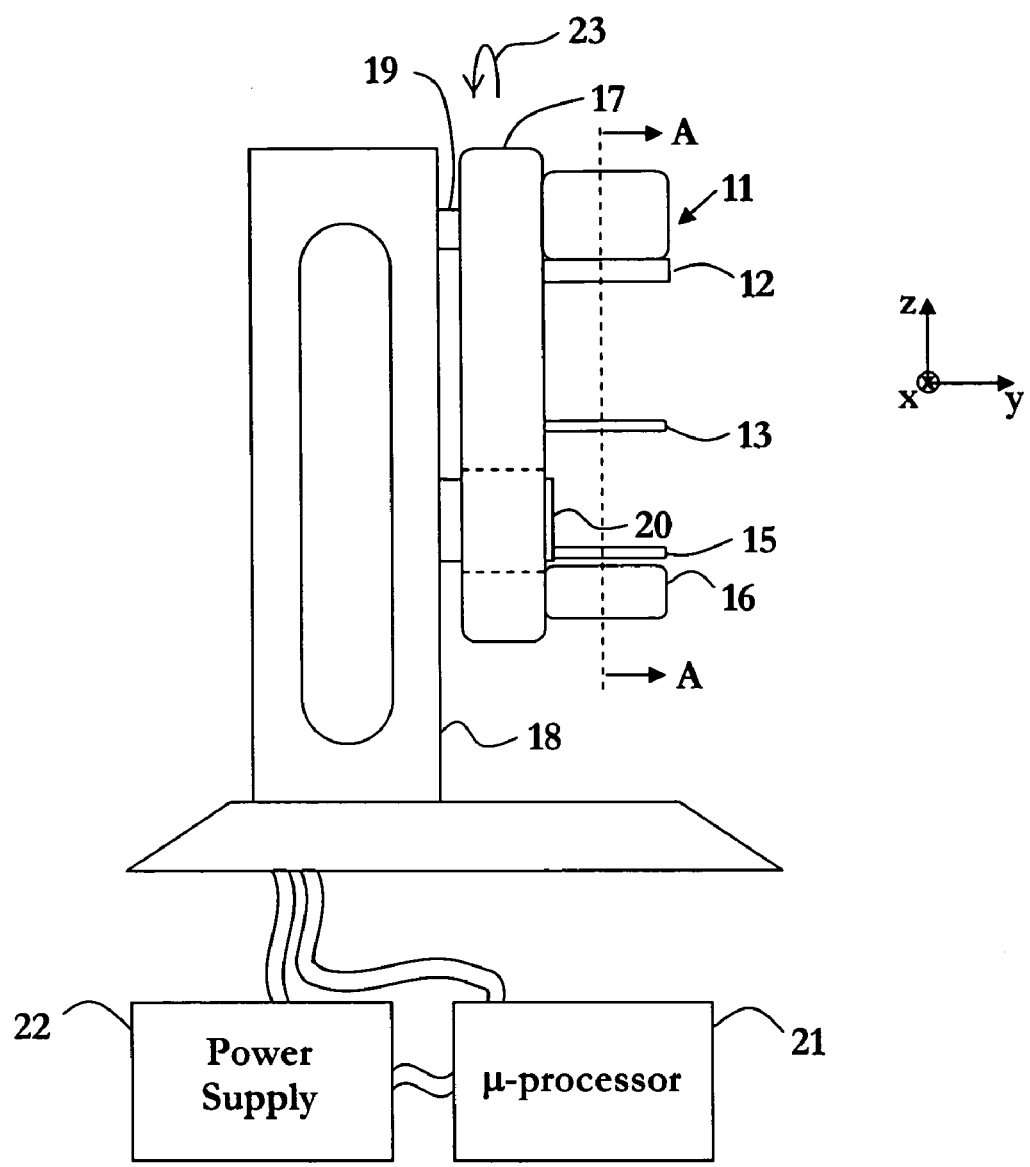
FIG. 1 illustrates schematically, in a side view, an apparatus for dual-source scanning-based X-ray imaging according to a preferred embodiment of the present invention.
Figure 2:
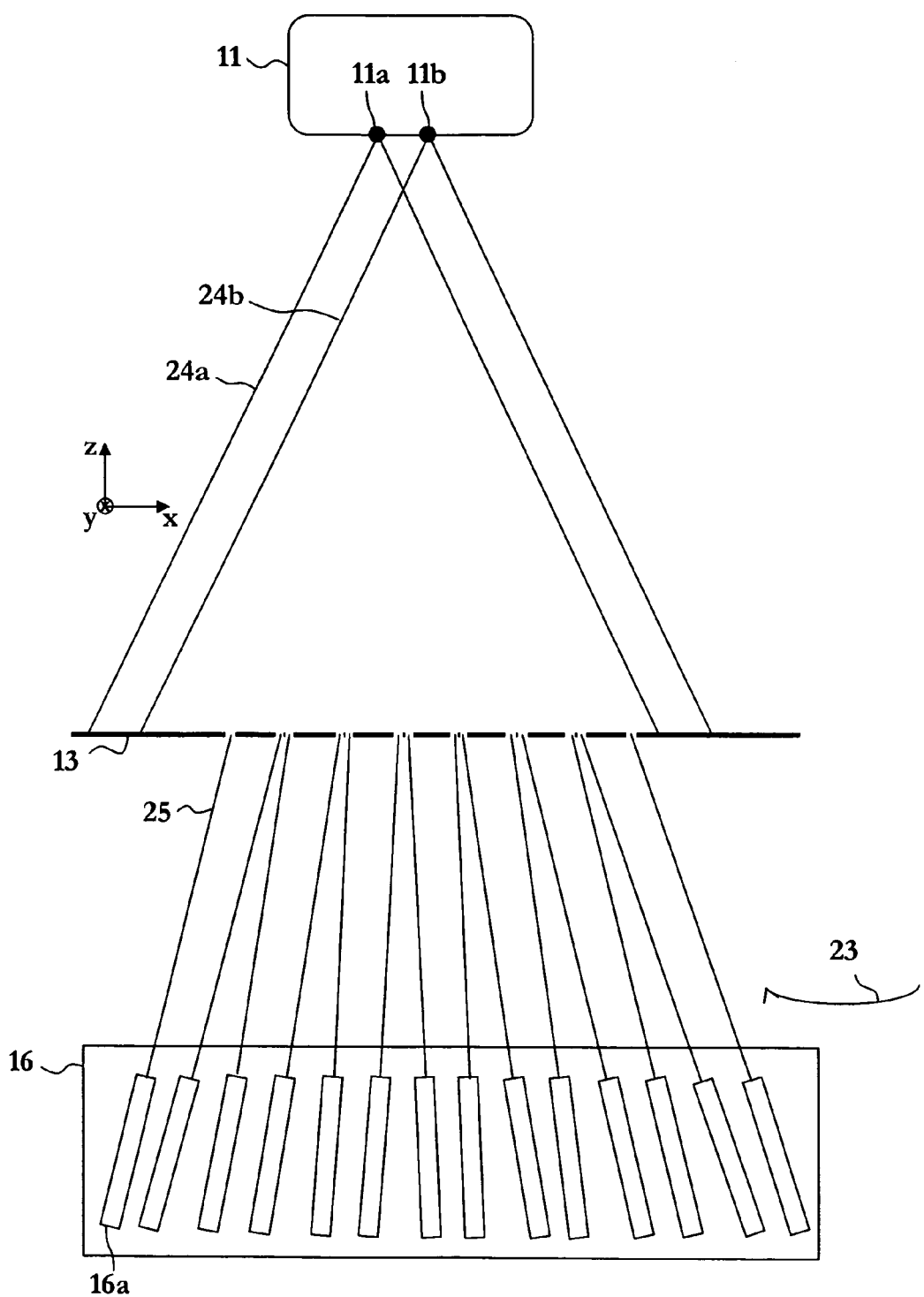
FIG. 2 is a schematic enlarged cross-sectional view of some of the components of the apparatus of FIG. 1 taken along the line A-A.

From top to bottom the apparatus shown in FIGS. 1-2 comprises a radiation or X-ray source arrangement 11, a fan beam collimator arrangement 13, an object table or holder 15, and a radiation detector 16.

The radiation source arrangement 11 comprises at least two radiation sources 11a-b, preferably X-ray tubes, each having a cathode, which emits electrons, and an anode, which emits X-rays in response to being struck by the electrons. The two X-ray tubes are provided for emitting radiation of equal or different energies centered around a respective symmetry line essentially parallel with the z axis. In FIG. 2 the radiation emitted by the radiation source 11a is indicated by reference numeral 24a, whereas the radiation emitted by the radiation source 11b is indicated by reference numeral 24b.

The radiation source arrangement 11 may further comprise a filter arrangement 12 just beneath the X-ray tubes, which typically includes thin metallic foils acting as filters to absorb the lowest (and sometimes also the highest) energy photons, which do not contribute significantly to the image quality. Preferably, the filter arrangement 12 has different filter sections in front of the different X-ray tubes so that different radiation from different X-ray tubes may be filtered differently. This filter arrangement 12 is typically optional, but may be required to provide radiation of different energies if the two radiation sources emit radiation of similar energy. The filter arrangement may alternatively be placed in or on the fan beam collimator 13. Reference is made to U.S. Pat. No. 7,027,561, the contents of which being hereby incorporated by reference.

The fan beam collimator 13, which is optional, may be a thin foil of e.g. tungsten with narrow radiation transparent slits etched away. The slits are aligned with corresponding line-shaped sensitive areas or entrance slits of the detector 16 so that X-ray bundles passing through the slits of the fan beam collimator 13 will reach the sensitive areas of the detector 16. The X-ray bundles are schematically indicated by 25 in FIG. 2. Yet optionally, a further collimator may be arranged in front of the detector (i.e. downstream of an object to be imaged).

The detector 16 comprises a plurality of direction sensitive line detectors 16a arranged in an array, each extending in the y direction in order to record one-dimensional images in the y direction. Each of the line detectors 16a is preferably a gaseous-based ionization detector, wherein electrons freed as a result of ionization by ionizing radiation entered into the line detector are accelerated, and optionally avalanche amplified, in a direction essentially perpendicular to the direction of the entered ionizing radiation. Such line detector is referred to as a gaseous-based edge-on detector.

Such line detectors and arrays thereof are further described in the following U.S. Patents issued to Tom Francke at al.: U.S. Pat. Nos. 6,337,482; 6,477,223; 6,476,397; 7,016,458; 7,006,597; 6,940,942; 6,970,533; 6,856,669; 6,873,682; 6,784,436; 6,794,656; 6,818,901; 6,627,897; 6,627,897; and 6,522,722, as well as in references therein, all of which being hereby incorporated by reference.

However, alternatively each of the line detectors 16a may be any of a scintillator-based detector, a PIN-diode array, a TFT array, a CCD array, a gaseous-based detector, a liquid-based detector, a solid-state detector, or a CMOS detector.

According to the invention, the line detectors 16a in the array are alternately pointing towards different ones of the two radiation sources 11a-b. That is, every second line detector is pointing towards the radiation source 11a and every second line detector is pointing towards the radiation source 11b.

The direction sensitivity of the line detectors imply that each of them measures only radiation from the radiation source, to which it is directed. Typically the opening angle of each line detector in the x direction may be as low as 0.1 degrees.

If the line detectors are gaseous-based edge-on detectors, each of them comprises readout strips that are essentially pointing towards either one of the radiation sources 11a-b. This means that the readout strips in each line detector are arranged in a fan-like structure, wherein the extension lines of the readout strips converge in either one of the radiation sources 11a-b.

The radiation source 11, the optional fan beam collimator 13 and the detector 16 are attached to a common E-arm 17, which in turn is rotatably attached to a vertical stand 18 by means of a spindle 19 approximately center of gravity of the E-arm arrangement, but can also be placed at any position within the E-arm arrangement. In this manner, the radiation source arrangement 11, the optional fan beam collimator 13 and the detector 16 can be moved in a common pivoting movement relative to an object to be examined arranged on the object table 15 to scan the object. The pivoting movement is schematically indicated by arrow 23, i.e. it is performed essentially in the x direction. The object table 15 is firmly attached to a support 20, which in turn is firmly attached to the vertical stand 18. For this purpose the E-arm 17 is provided with a recess or similar in the E-arm 17 (illustrated by the dashed lines). During scanning, the object is kept as still as possible.

Furthermore, the detector apparatus comprises a microprocessor or computer 21 provided with suitable software for controlling the apparatus and readout and post-processing of the data recorded by the line detector unit 16 and a power supply 22 for supplying the detector 16 and the microprocessor or computer 21 with power and for driving a step motor or similar housed in the vertical stand 18 for driving the spindle 19 and thus the E-arm 17.

During scanning, the line detectors 16a are kept aligned with the radiation sources 11a-b to enable each of the line detectors 16a to record a plurality of line images of the object. If the radiation sources 11a-b are provided for creating ionizing radiation of different energies, the scanning is preferably performed at least a distance corresponding to two times the distance between adjacent ones of the line detectors 16a, to thereby enable recording of line images sufficient to form a two-dimensional image of the object at each of the different energies.

The images may then be post-analyzed in the computer 21 to reveal information regarding the elemental composition of the detected object. This is a well described procedure in the literature. One common way is to operate one of the X-ray sources with a low energy spectrum, where more X-rays are photoelectrically absorbed than Compton scattered in a selected element in the object, e.g. calcium in bones. The second X-ray source is operated with a high X-ray energy spectrum, where more X-rays are Compton scattered in the object than are photoelectrically absorbed. The images from the two X-ray sources are then subtracted from one another giving a resulting image displaying the type of tissue one has selected, e.g. bone (calcium). With more than two sources several elements can be image-enhanced simultaneously using this method.

It shall be appreciated that the detector apparatus of FIG. 1 may be modified and arranged for linear movement, e.g. in the x direction, of the radiation source arrangement 11, the optional fan beam collimator 13 and the detector 16 with respect to the object being examined, as being described in the above cited U.S. Pat. No. 6,940,942.

Yet alternatively, the optional fan beam collimator 13 and the detector 16 may be rotated in the horizontal plane, i.e. the xy plane, with respect to the object being examined. Such rotational-based scanning is disclosed in the above cited U.S. Pat. No. 6,794,656.

It shall further be appreciated that the apparatus of FIG. 1 may instead be modified such that the object is moved during scanning, while the radiation source arrangement 11, the optional fan beam collimator 13 and the detector 16 are kept at rest.

It shall further be noted that the apparatus of FIGS. 1-2 may be equipped with more than two radiation sources. In the general case each of the radiation sources create radiation of different energies, the line detectors are alternately pointing towards different ones of the radiation sources, and the scanning is performed at least a distance corresponding to N times the distance between two adjacent ones of the line detectors, where N is the number of the radiation sources, to thereby enable recording of line images sufficient to form a two-dimensional image of the object at each of the different energies.

For a given array of line detectors and for a given scanning speed, the more radiation sources that are used, the more spectral information of the object is determined (which may be converted to information regarding the composition or elemental structure of the object), but the longer distance has to be scanned which results in more time-consuming measurements and less temporal resolution.

In one embodiment the distance between adjacent ones of the radiation sources is kept as short as possible so that the two-dimensional images recorded at different energies are recorded, pixel by pixel, from interactions in similar portions of the object.

Such embodiment may be used for bone and mineral density measurements in X-ray examinations of the breast or the upper part of the body of a patient. The radiation source arrangement may comprise one X-ray source producing X-ray radiation of an energy of about 30 keV and one X-ray source producing X-ray radiation of an energy of about 160 keV. Typically, the radiation source arrangement, the fan beam collimator and the detector are moved linearly relative to the patient (in the X direction of FIG. 2) to scan the patient. The scanning may be performed so that each line detector scans across the entire patient. For two-dimensional imaging applications oversampling is obtained, whereas the longer scanning is required for tomosynthesis applications.

However, in another embodiment the distance between adjacent ones of the radiation sources is kept longer to reveal more information of the object in depth, i.e. in the z direction, particularly if the recorded data is used in tomosynthesis. Thus, adjacent radiation sources are spaced apart by at least 0.2 degrees, preferably at least 5 degrees, more preferably at least 30 degrees, and most preferably at least 60 degrees, as seen from the detector 16. Here, scanning is performed a length which is sufficient for scanning each of the line detectors 16a across the entire object to obtain, for each of the line detectors 16a, a two-dimensional image of radiation as transmitted through the object in a respective one of a plurality of different angles. Such image data may be used in a tomosynthesis process in order to reconstruct two-dimensional images of the object in arbitrary planes and directions, and even three-dimensional images of the object.

In FIGS. 1-2, the radiation sources 11a-b are arranged spaced apart in the x direction, i.e. essentially in the scanning direction. However, this has not to be so.

Figure 3:
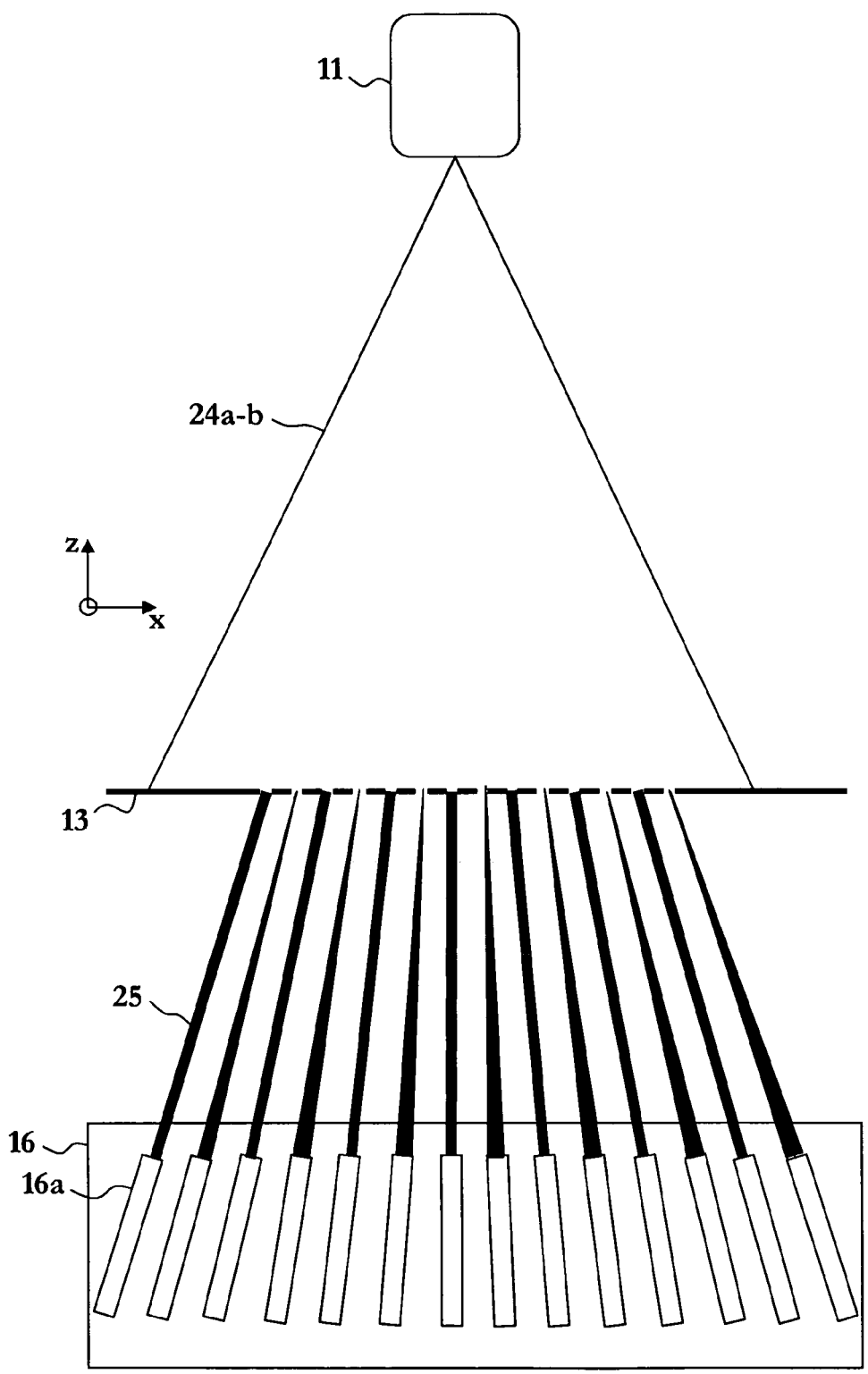
FIG. 3 is a schematic enlarged cross-sectional view of some of the components of an apparatus for dual-source scanning-based X-ray imaging according to a further embodiment of the invention.

In FIG. 3 a schematic enlarged cross-sectional view of some of the components of an apparatus for dual-source scanning-based X-ray imaging according to a further embodiment of the invention is shown. The cross-section is oriented in a similar manner as the one of FIG. 2.

The apparatus differs from the FIGS. 1-2 apparatus in that the radiation sources 11a-b are spaced apart in the y direction instead of in the x direction, that is the radiation sources 11a-b are arranged along a line, which is essentially perpendicular to the scanning direction (x direction) and essentially parallel with the extension of each of the line detectors (y direction).

The radiation source 11a is arranged in the plane of the cross section of FIG. 1 whereas the radiation source 11b is arranged behind the radiation source 11a. This means that all line detectors 16a are pointing towards the same x coordinate, but whereas every second line detector is pointing towards the y coordinate in the plane of the cross section of FIG. 1, every second line detector is pointing towards a y coordinate behind the plane of the cross section of FIG. 1. The "depth" in FIG. 1 is indicated by the shape of every second radiation bundle 25, i.e. every second radiation bundle 25 is coming from underneath the plane of the cross section of FIG. 1 and becomes thicker the closer it comes to the detector 16 and the plane of the cross section of FIG. 1. The thickness variation is of course highly exaggerated in the Figure for illustrative purposes.

It shall be appreciated that the radiation sources may be spaced apart in other directions as well, e.g. in the scanning direction and in a direction perpendicular thereto such as in the x and y directions.

In one application the above scanning is used for full body examinations of a patient. The radiation sources are spaced apart substantially at least in the y direction. They may be spaced apart as much as 90 degrees as seen from the patient. Preferably, both radiation sources produce X-ray radiation of the same energy (but they may be arranged to produce X-ray radiation of different energies, e.g. in a complementary measurement). Typically, the radiation source arrangement, the fan beam collimator and the detector are held still whereas the patient is moved linearly (in the x direction of FIG. 3) to scan the entire patient.

Figure 4:
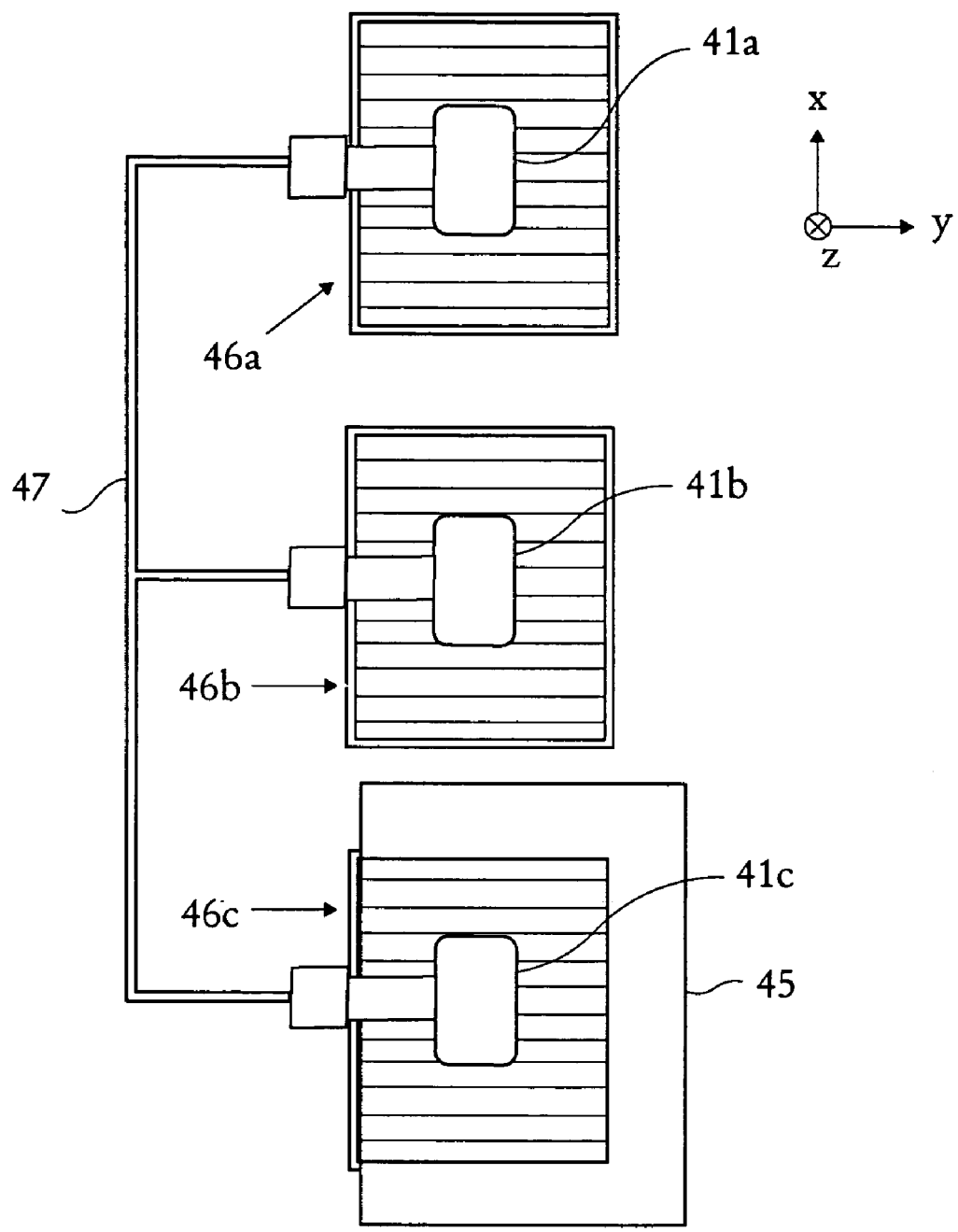
FIGS. 4 and 5 are each a schematic top plan view of an apparatus for dual-energy scanning-based X-ray imaging according to yet a further embodiment of the invention.

With reference next to FIG. 4, which is a schematic top plan view of an apparatus for dual-energy scanning-based X-ray imaging, a yet further embodiment of the invention will be described.

The apparatus comprises three radiation sources 41a-c provided for emitting ionizing radiation and a plurality of direction sensitive line detectors arranged in three arrays 46a-c, all rigidly connected together by a support structure 47. The apparatus may also comprise three fan beam collimator arrangements as indicated in the Figure. The three radiation sources 41a-c, the line detectors in the three arrays 46a-c, and the optional three fan beam collimator arrangements are scanned in the x direction as a unit, while a fixedly arranged object table or holder 45 is holding an object to be examined, to record line images of the object.

According to the invention, the radiation sources are provided for emitting ionizing radiation of different energies, the line detectors in a first one 46a of the arrays are pointing towards a first one 41a of the radiation sources, the line detectors in a second one 46b of the arrays are pointing towards a second one 41b of the radiation sources, and the line detectors in the third one 46c of the arrays are pointing towards the third one 41c of the radiation sources. During scanning the line detectors are kept aligned with the respective radiation sources 41a-c to enable each of the line detectors to record a plurality of line images of the object. The scanning is performed so that each of the line detectors is scanned across the entire object to thereby enable recording of line images sufficient to form multiple two-dimensional images of the object at each of the different energies.

If each of the arrays comprises M line detectors, the scan result in M two-dimensional images for each of the three different radiation source energies.

Figure 5:
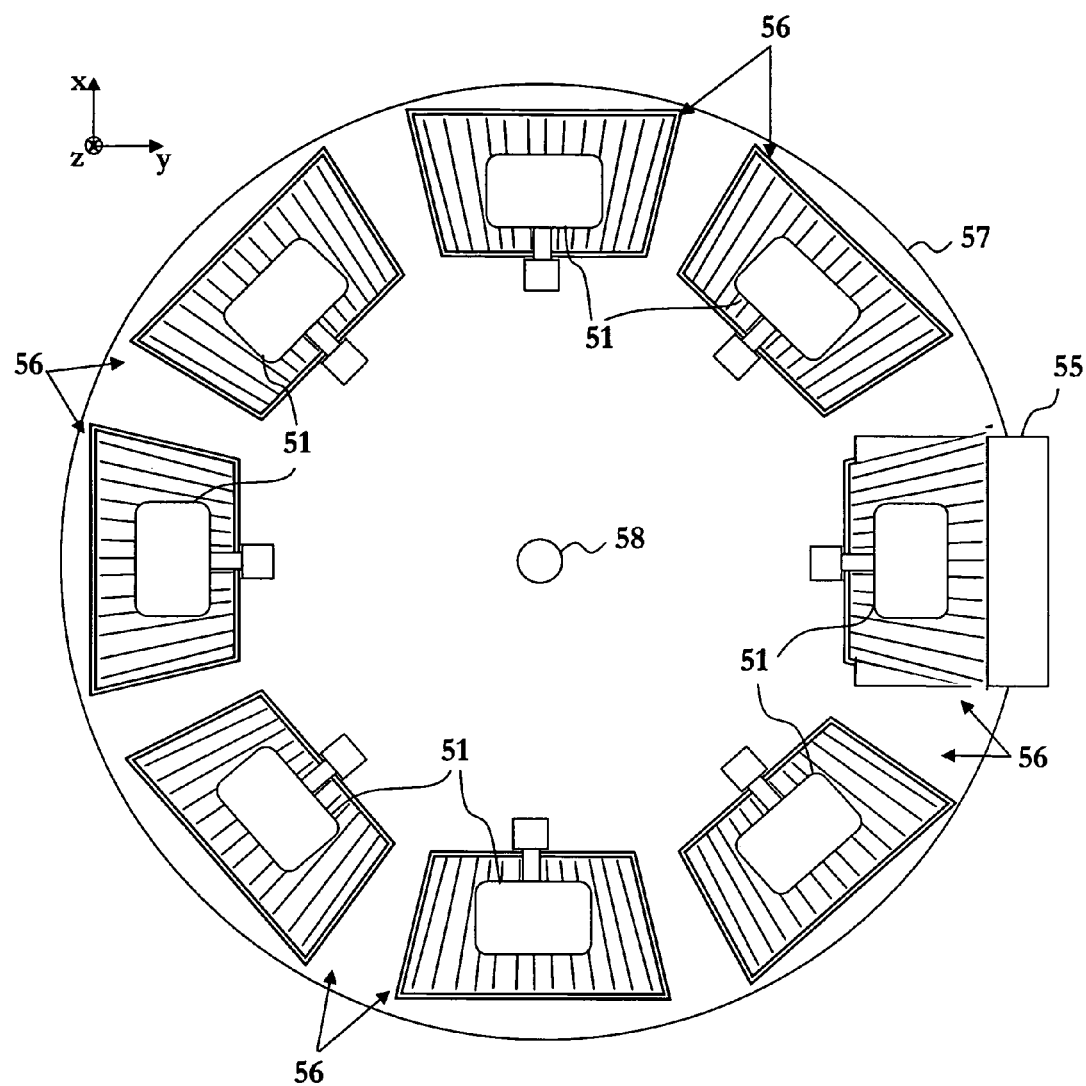

In FIG. 5 a still further embodiment of the invention is shown. Here, eight radiation sources 51 provided for emitting ionizing radiation and a plurality of direction sensitive line detectors arranged in eight arrays 56 are rigidly connected together by a support structure 57. The apparatus may also comprise eight fan beam collimator arrangements as indicated in the Figure. The eight radiation sources 51, the line detectors in the eight arrays 56, and the optional eight fan beam collimator arrangements are scanned in the xy plane in a rotational movement around an axis 58, while a fixedly arranged object table or holder 55 is holding an object to be examined, to record line images of the object.

According to the invention, the radiation sources are provided for emitting ionizing radiation of different energies, the line detectors in each of the arrays 56 are pointing towards a respective one of the radiation sources 51. During scanning the line detectors are kept aligned with the respective radiation sources 51 to enable each of the line detectors to record a plurality of line images of the object. The scanning is at least performed one full revolution so that each of the line detectors is scanned across the entire object to thereby enable recording of line images sufficient to form multiple two-dimensional images of the object at each of the different energies.

If each of the arrays comprises M line detectors, the scan result in M two-dimensional images for each full revolution of scanning and for each of the eight different radiation source energies.

It shall be appreciated that the embodiments of FIGS. 4 and 5 may be modified to comprise any number of radiation sources, arrays of line detectors, and optional collimator arrangements, as long as there are at least two of them. These embodiments are particularly advantageous in applications where several two-dimensional images shall be taken to record a process or a periodic phenomenon temporally resolved.

Depending on requirements on spectral and temporal resolutions the embodiments of FIGS. 4 and 5 may comprise a larger number of radiation sources where only some of them create radiation of different energies in order to increase the temporal resolution to the cost of the spectral resolution. For instance, in the FIG. 5 embodiment every fourth radiation source may create radiation of the same energy. Thus the number of images at each energy is increased by a factor of two, whereas the number of different energies, at which images are recorded, is reduced by a factor of two.

It shall be appreciated that U.S. patent publications Nos. 2005/0226367 A1 and US 2005/0226368 A1 (inventor: Tom Francke) disclose high-speed detectors that may be used in the present invention after certain modifications, the contents of which publications being hereby incorporated by reference.

It shall be appreciated that the various embodiments of the present invention may be combined to reach still further embodiments of the invention. Various features and details as specified in some of the embodiments of the invention may be equally applicable in other ones of the embodiments.

What is claimed is:

1. A dual-source scanning-based radiation detecting apparatus comprising
   at least two radiation sources provided for emitting ionizing radiation;
   a plurality of direction sensitive line detectors arranged in an array; and
   a device for scanning said line detectors across an object to be examined, wherein
   the line detectors in said array are alternately pointing towards different ones of said radiation sources; and
   said device for scanning is arranged for keeping said line detectors aligned with said radiation sources during scanning to enable each of said line detectors to record a plurality of line images of said object.

2. The apparatus of claim 1 wherein
said radiation sources are provided for creating ionizing radiation of different energies; and
said device for scanning is arranged for scanning at least a distance corresponding to N times the distance between two adjacent ones of said line detectors, where N is the number of said radiation sources, to thereby enable recording of line images sufficient to form a two-dimensional image of said object at each of said different energies.

3. The apparatus of claim 1 wherein said device for scanning is arranged for scanning a length which is sufficient for scanning each of the line detectors across the entire object to obtain, for each of the line detectors, a two-dimensional image of radiation as transmitted through the object in a respective one of a plurality of different angles.

4. The apparatus of claim 1 wherein the number of said radiation sources is two.

5. The apparatus of claim 1 wherein the number of said radiation sources is three or higher.

6. The apparatus of claim 1 wherein each of said line detectors is a gaseous-based ionization detector, wherein electrons freed as a result of ionization by ionizing radiation entered into the line detector are accelerated, and optionally avalanche amplified, in a direction essentially perpendicular to the direction of the entered ionizing radiation.

7. The apparatus of claim 6 wherein each of said line detectors comprises readout strips that are essentially pointing towards either one of said radiation sources.

8. The apparatus of claim 1 wherein each of said line detector is any of a scintillator-based detector, a PIN-diode array, a TFT array, a CCD array, a gaseous-based detector, a liquid-based detector, a solid-state detector, or a CMOS detector.

9. The apparatus of claim 1 wherein adjacent ones of said radiation sources are spaced apart by at least 0.2 degrees as seen from the detecting apparatus.

10. The apparatus of claim 1 wherein adjacent ones of said radiation sources are spaced apart by at least 5 degrees as seen from the detecting apparatus.

11. The apparatus of claim 1 wherein adjacent ones of said radiation sources are spaced apart by at least 30 degrees as seen from the detecting apparatus.

12. The apparatus of claim 1 wherein adjacent ones of said radiation sources are spaced apart by at least 60 degrees as seen from the detecting apparatus.

13. The apparatus of claim 1 wherein said radiation sources are arranged along a line, which is essentially parallel with the scanning direction.

14. The apparatus of claim 1 wherein said radiation sources are arranged along a line, which is essentially perpendicular to the scanning direction.

15. The apparatus of claim 14 wherein said line is essentially parallel with the extension of each of said line detectors.

16. The apparatus of claim 1 wherein said radiation sources are spaced apart in the scanning direction and in a direction perpendicular thereto.

17. A method for dual-source scanning-based radiation detection comprising the steps of:
creating ionizing radiation of different energies by at least two radiation sources;
passing said ionizing radiation of different energies through an object under examination;
detecting ionizing radiation of different energies after having passed through the object by a plurality of direction sensitive line detectors arranged in an array, wherein the line detectors in said array are alternately pointing towards different ones of the radiation sources; and
scanning said line detectors across the object while said line detectors are kept aligned with the radiation sources to enable each of said line detectors to record a plurality of line images of the object, wherein the scanning is performed at least a distance corresponding to N times the distance between two adjacent ones of said line detectors, where N is the number of said radiation sources, to thereby enable recording of line images sufficient to form a two-dimensional image of said object at each of said different energies.

18. The method of claim 17 wherein the ionizing radiation of different energies is created by two radiation sources.

19. The method of claim 17 wherein the ionizing radiation of different energies is created by radiation sources distanced from each other by at least 0.2 degrees as seen from said array.

20. The method of claim 17 wherein the ionizing radiation of different energies is created by radiation sources distanced from each other by at least 5 degrees as seen from said array.

21. The method of claim 17 wherein the ionizing radiation of different energies is created by radiation sources distanced from each other by at least 30 degrees as seen from said array.

22. The method of claim 17 wherein the ionizing radiation of different energies is created by radiation sources distanced from each other by at least 60 degrees as seen from said array.

23. The method of claim 17 wherein the ionizing radiation of different energies is created by radiation sources arranged along a line, which is essentially parallel with the scanning direction.

24. The method of claim 17 wherein the ionizing radiation of different energies is created by radiation sources arranged along a line, which is essentially perpendicular to the scanning direction.

25. A dual-energy scanning-based radiation detecting apparatus comprising
at least two radiation sources provided for emitting ionizing radiation;
a plurality of direction sensitive line detectors arranged in at least two arrays; and
a device for scanning said line detectors across an object to be examined, wherein
said at least two radiation sources are provided for creating ionizing radiation of different energies;
the line detectors in a first one of said at least two arrays are pointing towards a first one of said at least two radiation sources and the line detectors in a second one of said at least two arrays are pointing towards a second one of said at least two radiation sources;
said device for scanning is during scanning provided for keeping said line detectors aligned with said at least two radiation sources to enable each of said line detectors to record a plurality of line images of said object; and
said device for scanning is provided for scanning each of said line detectors across the entire object to thereby enable recording of line images sufficient to form multiple two-dimensional images of said object at each of said different energies.

26. A method for dual-energy scanning-based radiation detection comprising the steps of:
- creating ionizing radiation of different energies by at least two radiation sources;
- passing said ionizing radiation of different energies through an object under examination;
- detecting ionizing radiation of different energies after having passed through the object by a plurality of direction sensitive line detectors arranged in at least two arrays; and
- scanning said line detectors across an object to be examined while the line detectors in a first one of said at least two arrays are kept aligned pointing towards a first one of said at least two radiation sources and the line detectors in a second one of said at least two arrays are kept aligned pointing towards a second one of said at least two radiation sources to enable each of said line detectors to record a plurality of line images of said object, wherein each of said line detectors is scanned across the entire object to thereby enable recording of line images sufficient to form multiple two-dimensional images of said object at each of said different energies.

* * * * *